United States Patent [19]

De Haen et al.

[11] Patent Number: 5,772,651
[45] Date of Patent: Jun. 30, 1998

[54] CONTAINER FOR DIAGNOSTIC CONTRAST COMPOSITIONS

[75] Inventors: Christoph De Haen, Milan; Valtero Canepa, Savona, both of Italy

[73] Assignee: Dibra S.P.A., Milan, Italy

[21] Appl. No.: 448,474

[22] PCT Filed: Jan. 3, 1995

[86] PCT No.: PCT/EP95/00006

§ 371 Date: May 25, 1995

§ 102(e) Date: May 25, 1995

[87] PCT Pub. No.: WO95/19199

PCT Pub. Date: Jul. 20, 1995

[30] Foreign Application Priority Data

Jan. 18, 1994 [IT] Italy .................................. MI94A0055

[51] Int. Cl.$^6$ .................................................... A61B 19/00
[52] U.S. Cl. ............................. 604/403; 604/415; 222/92
[58] Field of Search ..................................... 604/408, 410, 604/415, 403; 222/92

[56] References Cited

U.S. PATENT DOCUMENTS

| 4,516,977 | 5/1985 | Herbert .................................... 604/415 |
| 4,899,911 | 2/1990 | Rohde et al. .............................. 222/92 |
| 5,129,894 | 7/1992 | Sommermeyer et al. ............... 604/410 |

FOREIGN PATENT DOCUMENTS 3200264  7/1983  Germany .............................. 604/415

Primary Examiner—Robert A. Clarke
Attorney, Agent, or Firm—Bucknam and Archer

[57] ABSTRACT

A packaging ready for the use for the oral administration of air-free diagnostic contrast solutions or suspensions comprising an air-tight collapsible container, equipped with a distributing beak with a sealing detachable cap, containing a diagnostic degassed aqueous composition.

10 Claims, 1 Drawing Sheet

CONTAINER FOR DIAGNOSTIC CONTRAST COMPOSITIONS

This application claims the benefit of international application PCT/EP95/00006 filed Jan. 3, 1995.

FIELD OF THE INVENTION

This invention relates to a container containing degassed aqueous compositions for the oral air-free administration of the same.

DESCRIPTION OF THE PRIOR ART

Examination of the gastro-intestinal tract is often made difficult by the presence of gases which prevent the homogeneous distribution of the contrastographic compositions in the interior of the digestive tract. This is particularly true when ultrasonic echography of the stomach is to be performed.

Large gas volumes act as a reflecting surface for the ultrasonic waves thus darkening the nearby walls. Gas bubbles act similarly, reducing the view of the walls of stomach, duodenum and closely located structures. The use of water has been proposed to replace the gases in the stomach in order to improve the echographic view of the stomach and the other closely located organs, such as the pancreas (Crade M. et al., Am. J. Radiol. 131, 348, 1978; Fleischer et al., Am. J. Radiol. 136, 887, 1981).

For the same purpose, water containing D-sorbitol has been proposed (Hiroka et al., J. Clin. Ultrasound 17, 585, 1989). In this case, water has been previously heated to become gas-free.

WO 91/18612, published on Dec. 12, 1991, proposes the use of aqueous solutions containing biocompatible polymers which can be mixed with a compound containing silica. Unfortunately the results could not be fully reproduced since the liquid ingestion from an open container, such as a glass also brings about the ingestion of air. The quantity of ingested air varies from one individual to another. The ingested air can partly destroy the effect of enhanced echographic transparency which derives from water administration. In addition, tap water and the water left in an open container become saturated with air. Water is heated in the stomach, causing the development of air which produces bubbles. These bubbles can mar some of the positive effects on the echographic images generated by water ingestion.

SUMMARY OF THE INVENTION

This invention overcomes the above mentioned drawbacks, by supplying packages ready to be used comprising an air-tight, collapsible container, equipped with an erogating beak sealed with a detachable cap and containing a degassed aqueous diagnostic solution or suspension.

This invention is also useful for packaging air sensitive diagnostic contrast media, such as for instance, solutions containing salts and/or oxidizable paramagnetic metal ion complexes, in particular $Mn^{2+}$, $Fe^{2+}$, $Co^{2+}$, $Eu^{2+}$ and $V^{3+}$.

Moreover the invention is also applicable to the packaging of diagnostic formulations for the examination of the digestive tract by using X-ray and MRI techniques. These compositions for example may be solutions or suspensions of iodinated compounds, paramagnetic chelate complexes, ferromagnetic and or superparamagnetic metal derivatives or opacifying compounds such as for instance, $BaSO_4$. Obviously these compositions may also be formulated with the addition of suitable additives and excipients, such as viscosity enhancers, sweeteners and so on usually employed for the formulation of gastro-intestinal preparations.

The packages of this invention allow the administration of degassed diagnostic compositions without the simultaneous ingestion of air since the patient drinks from the container which is squeezed directly into the oral cavity, avoiding contact between the latter and the environment air.

Figure 1:
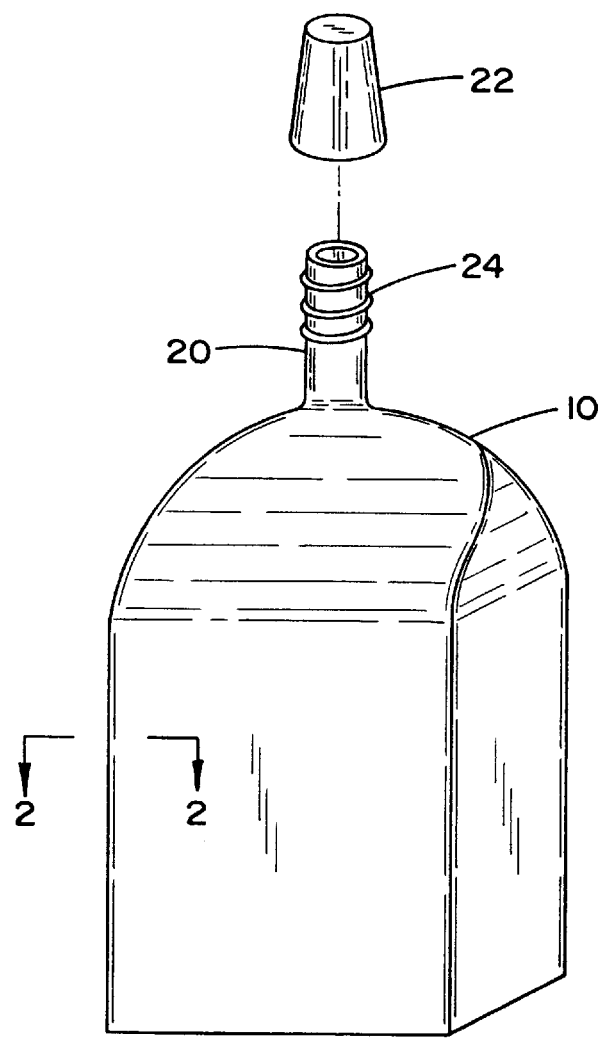
FIG. 1 is a perspective elevational view of a container according to the present invention.
Figure 2:
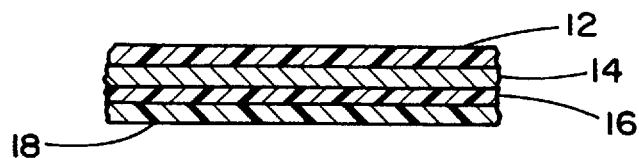
FIG. 2 is a partial cross sectional view of the container of FIG. 1 taken along the line 2—2 of FIG. 1.

Turning to the drawings, in FIG. 1 there is shown a container 10 is filled with the solution or suspension. The container may be made of any material but preferably of a material compatible with heat sterilization conditions, the sterilization preferably being carried by means of vapor at 121° C. or with gamma-ray sterilization. Suitable materials include for instance polyethylene, polyesters and in some cases aluminum. Preferably, as clearly seen in FIG. 2, the container is made of rolled plastic characterized by an inner layer 12 compatible with water and other possible ingredients, preferably of polyethylene, a metallic layer 14, preferably aluminum, protecting the internal part from light, a second layer 16 of polyethylene followed by an external plastic layer 18 providing mechanical resistance, preferably a polyester. The collapsible container may be prepared by soldering the rolled plastic sheets, previously folded in a shape which is flat when the container is empty and is swellable when filled with the diagnostic solution or suspension. The container is capable of containing from 50 ml to 2 l, preferably between 250 ml and 1 l of diagnostic solution or suspension. These containers are known and available on the market, as for EP 510388 published on Oct. 28, 1992.

The containers described in the above mentioned patent application EP 510388, which can be used in this invention, include a beak 20 connected to the container 10 consisting of a tubular structure with an internal diameter between 2 and 14 mm, preferably between 4 and 10 mm. This tubular structure crosses the container walls and the junction of the wall to the beak is air-tight sealed. This air-tight junction may be equipped with fins, in correspondence with the external side of the junction. At the external tip of the beak there is an air-tight detachable locking device, preferably a screw cap 22, which may be sealed by engagement with threads 24 on beak 20. The tubular structure of the beak has some openings near its upper tip, the openings being in the interior of the container wall, these openings being from 0.3 to 5 times, preferably from 1 to 1.2 times, bigger than the cross section of the tube calibre and are extended up to the junction between the tube and the wall of the container. The tubular structure of the beak penetrates the interior of the container up to a length equivalent to 5–75%, preferably 30–60% of the total length of the container.

As various changes could be made in materials, shape and size without departing from the scope of the invention, it is intended that all matter contained in the above description shall be interpreted as illustrative and not in a limiting sense.

EXAMPLE 1

Under air-tight conditions, a degassed aqueous solution of D-sorbitol 0.3M is prepared. The solution passes from the container in which it has been placed in solution to the filling machine through the tubes without any air contact. The machine prepares Guala-Pack$^R$ packages of 500 ml, hermetically sealed, totally filled with liquid. The product is sterilized in an autoclave at 121° C. for 20 minutes.

EXAMPLE 2

Following the same procedure of Example 1 packages of 250, 500 and 1000 ml of degassed pure water are produced.

EXAMPLE 3

The formulations of a contrast medium for echography described in WO 91/18612 (E. Unger) are prepared under vacuum as described in Example 1 with Guala-Pack$^R$ packages of 200 and 500 ml. The sealed product is sterilized with gamma rays of 1–5 Mrad according to the total bacterial charge of the solution.

EXAMPLE 4

Gastromiro$^R$ is a contrast medium designed for X-ray examination of the digestive tract either by the oral or by the rectal route (enema) and in Computed Tomography (CT) as an oral agent for the outlining of the digestive tract in the diagnosis of the abdomen.

Gastromiro$^R$ composition contains (for 100 ml of solution):

| | |
|---|---|
| Iopamidol (active iodinated component) | 61.24 gs |
| Orange flavor | 220 mgs |
| Sodium cyclamate | 150 mgs |
| Red curacao flavor | 110 mgs |
| Disodium edetate dihydrate | 30 mgs |
| Saccharin | 13.4 mgs |
| Citric acid monohydrate | 5.5 mgs |
| Sodium hydroxide | 2.93 mgs |
| Water for injections q.s. to | 100 ml |

A solution according to this composition was prepared and transferred in Guala-Pack$^R$ packages of 100 and 200 ml following the procedure of Example 1.

For CT scanning 200 ml of the preceding solution were diluted to 5000 ml with water for injections. The resulting solution was transferred in Guala-Pack$^R$ packages of 500 ml following the procedure of Example 1.

EXAMPLE 5

Enteral Magnevist$^R$ is a contrast medium for gastro-intestinal MRI examinations.

Composition (for 10 ml of solution):

| | |
|---|---|
| Dimeglumin gadopentetate (Gd-DTPA/dimeg) | 94 mgs |
| Sodium-DTPA | 45.5 mgs |
| Sodium citrate dihydrate | 753.5 mgs |
| Mannitol | 1500 mgs |
| Water q.s. to | 10 ml |

A solution according to this composition was prepared and transferred in Guala-Pack$^R$ packages of 500 ml following the procedure of Example 1.

EXAMPLE 6

A solution 0.1 mM of Prohance (Gadolinium(III) (1,4,7-tris(carboxymethyl)-10-(2'-hydroxypropyl)-1,4,7,10-tetraazacyclododecane: EP 292689) was prepared and transferred in Guala-Pack$^R$ packages of 100, 250 and 500 ml, following the procedure of Example 1.

EXAMPLE 7

A solution 0.1 mM of di-sodium Gd-BOPTA, (Gadolinate (2-),(4R,S)-[4-carboxy-5,8,11-tris (carboxymethyl)-1-phenyl-2-oxa-5,8,11-triazatridecan-13-oate (5$^-$)] di-sodium (2+) salt: EP 230893) was prepared and transferred into Guala-Pack$^R$ packages of 100, 250 and 500 ml, following the procedure of Example 1.

EXAMPLE 8

Ferric Ammonium Citrate formulations 2.4 g of ferric ammonium citrate were dissolved in 1500 ml of water with the addition of 180 mgs of aspartame and 12 mgs of grape flavor. The resulting solution was transferred in GualaPack$^R$ packages of 500 ml, following the procedure of Example 1. This formulation is particularly useful for MR examinations of the upper abdomen.

EXAMPLE 9

Suspensions of paramagnetic/superparamagnetic oral contrast media for magnetic resonance tomography.

Magnetite nanoparticles suspensions analogous to those obtained with Abdoscan$^R$ (Nycomed) were prepared containing 94 mgs Fe, viscosity enhancing agents up to 24 gs, aspartame as sweetener in 1000 ml of water and transferred into 500 ml Guala-Pack$^R$ packages following the procedure of Example 1.

Magnetite particles suspensions according to Lumirem$^R$ (Guerbet), i.e. containing: 0.175 mgs Fe; 29.25 mgs sorbitol (70%), color (paraorange), preservatives (methyl-, ethyl-, propyl-paraoxybenzoate), NaCl, NaOH q.s., purified water up to 1 ml, were prepared. 5000 ml of a suspension according to the above composition were transferred in 500 ml Guala-Pack$^R$ packages following the procedure of Example 1.

EXAMPLE 10

Suspensions of Barium sulphate (BaSO$_4$) Prontobario$^R$ 60% (Bracco) suspensions were prepared according to the following composition:

| | |
|---|---|
| Barium sulfate | 60 gs |
| Xanthan gum | 0.26 gs |
| Strawberry flavoring | 0.15 gs |
| Sodium benzoate | 0.12 gs |
| Dimethylpolysiloxane | 0.10 gs |
| Vanilla and cream flavoring | 0.03 gs |
| Citric acid monohydrate | 0.02 gs |
| Sodium saccharin dihydrate | 0.01 gs |
| Sulfuric acid 15% | q.s. to pH 4.5 |
| Purified water | q.s. to 100 ml |

Packages of Guala-Pack$^R$ from 250 to 500 ml were prepared following the procedure of Example 1.

I claim:

1. A packaging containing a diagnostic degassed contrast aqueous composition, said composition being in the form of an air-free aqueous solution or suspension for use for oral administration of said air-free diagnostic contrast solution or suspension, said packaging comprising an air-tight collapsible container, equipped with a distributing beak having a sealing detachable cap, said diagnostic contrast composition containing an iodinated X-ray opacifying compound, said diagnostic contrast composition containing, as a contrast agent, an echographic reflecting agent or pure water.

2. The packaging according to claim 1, wherein the diagnostic composition contains, as a contrast agent, a paramagnetic chelate complex for magnetic resonance imaging or superparamagnetic particles.

3. The package according to claim 1, wherein said opacifying compound is $BaSO_4$.

4. The packaging according to claim 1, wherein the container is made of rolled plastic and consists of the following layers a)–d):
  a) an internal layer compatible with water and with ingredients other than said diagnostic composition;
  b) a metal layer, which protects the interior of said container from light;
  c) a second layer formed by the same material as a);
  d) an external plastic layer to supply the mechanical resistance.

5. The packaging according to claim 4, wherein layers a) and c) are made of polyethylene, layer b) is made of aluminum, layer d) is made of a polyester.

6. The packaging according to claim 5, wherein said polyethylene, aluminum and polyester are compatible with vapor sterilization at 121° C. or gamma rays sterilization.

7. The packaging according to claim 1, containing 50 ml up to 2 l of said diagnostic composition.

8. The packaging according to claim 1, wherein the contrast agent is degassed pure water.

9. The packaging according to claim 1, wherein said detachable cap is a screw cap.

10. The packaging according to claim 9, wherein said container has a wall and a length, said beak joins with said wall at a junction point, openings are provided in the interior of said wall up to said junction point and said beak penetrates the interior of said container to an extent of 30–60% of said total length of said container.

* * * * *